United States Patent
Liu et al.

(10) Patent No.: US 10,156,488 B2
(45) Date of Patent: Dec. 18, 2018

(54) PRISM-COUPLING SYSTEMS AND METHODS FOR CHARACTERIZING CURVED PARTS

(71) Applicant: CORNING INCORPORATED, Corning, NY (US)

(72) Inventors: Anping Liu, Horseheads, NY (US); Rostislav Vatchev Roussev, Painted Post, NY (US); Robert Anthony Schaut, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 1471 days.

(21) Appl. No.: 14/013,481

(22) Filed: Aug. 29, 2013

(65) Prior Publication Data

US 2015/0066393 A1    Mar. 5, 2015

(51) Int. Cl.
*G01L 1/24* (2006.01)
*G01N 21/23* (2006.01)
*G01N 21/41* (2006.01)

(52) U.S. Cl.
CPC .............. *G01L 1/24* (2013.01); *G01L 1/241* (2013.01); *G01N 21/23* (2013.01); *G01N 21/4133* (2013.01)

(58) Field of Classification Search
CPC .... G01B 11/16; G01B 11/14; B23K 26/0608; G01D 5/28; B29C 47/0019; G02B 6/34; G01N 21/553
USPC ...... 356/35, 492; 362/330, 237; 250/559.29; 349/58; 385/32; 436/164
See application file for complete search history.

(56) References Cited

U.S. PATENT DOCUMENTS

| | | | |
|---|---|---|---|
| 3,308,394 A | 3/1967 | Snitzer et al. | |
| 3,433,611 A | 3/1969 | Saunders et al. | |
| 3,873,209 A | 3/1975 | Schinke et al. | |
| 3,883,221 A | 5/1975 | Rigrod | |
| 4,207,000 A | 6/1980 | Miller | |

(Continued)

FOREIGN PATENT DOCUMENTS

| JP | 5531944 | 2/1980 |
|---|---|---|
| JP | 57157130 | 9/1982 |

(Continued)

OTHER PUBLICATIONS

Chiang, "Refractive-Index Profiling of Graded-Index Planar Waveguides from Effective Indexes Measured for Both Mode Types and at Different Wavelengths", pp. 827-832.*

(Continued)

*Primary Examiner* — Regis Betsch
*Assistant Examiner* — Kaleria Knox
(74) *Attorney, Agent, or Firm* — John T. Haran

(57) ABSTRACT

Prism coupling systems and methods for characterizing curved parts are disclosed. A coupling surface of a coupling prism is interfaced to the curved outer surface of the curved part to define a coupling interface. Measurement light is directed through the coupling prism and to the interface, wherein the measurement light has a width of 3 mm or less. TE and TM mode spectra reflected from the interface are digitally captured. These mode spectra are processed to determine at least one characteristic of the curved part, such as the stress profile, compressive stress, depth of layer, refractive index profile and birefringence.

20 Claims, 11 Drawing Sheets

(56) References Cited

U.S. PATENT DOCUMENTS

| | | | |
|---|---|---|---|
| 4,353,649 A | | 10/1982 | Kishii |
| 4,637,684 A | | 1/1987 | Tomita et al. |
| 4,655,589 A | * | 4/1987 | Cestaro .................. G01L 1/241 |
| | | | 356/35 |
| 5,164,589 A | | 11/1992 | Sjodin |
| 5,446,534 A | | 8/1995 | Goldman |
| 5,953,125 A | * | 9/1999 | de Groot ................ G01B 11/14 |
| | | | 356/492 |
| 6,459,492 B1 | * | 10/2002 | Hercher .................. G01D 5/28 |
| | | | 250/559.29 |
| 6,731,388 B1 | | 5/2004 | Simon et al. |
| 7,193,719 B2 | | 3/2007 | Meehan et al. |
| 7,701,529 B2 | * | 4/2010 | Kogure ............... B29C 47/0019 |
| | | | 349/58 |
| 8,281,510 B2 | * | 10/2012 | Yoshimura ............. G02B 5/124 |
| | | | 362/330 |
| 8,957,374 B2 | | 2/2015 | Liu et al. |
| 9,109,881 B2 | | 8/2015 | Roussev et al. |
| 9,140,543 B1 | * | 9/2015 | Allan ..................... G01B 11/16 |
| 2010/0028607 A1 | | 2/2010 | Lee et al. |
| 2011/0171746 A1 | * | 7/2011 | Fontaine .............. G01N 21/553 |
| | | | 436/164 |
| 2012/0106164 A1 | | 5/2012 | Michaelis et al. |
| 2012/0257387 A1 | * | 10/2012 | Kuchibhotla ...... B23K 26/0608 |
| | | | 362/237 |
| 2014/0092377 A1 | | 4/2014 | Liu et al. |
| 2014/0118740 A1 | | 5/2014 | Fontaine et al. |
| 2014/0368808 A1 | | 12/2014 | Roussev et al. |
| 2015/0066393 A1 | | 3/2015 | Liu et al. |
| 2015/0116713 A1 | | 4/2015 | Roussev et al. |
| 2015/0338308 A1 | | 11/2015 | Li et al. |

FOREIGN PATENT DOCUMENTS

| | | |
|---|---|---|
| JP | 04310836 | 11/1992 |
| JP | 6332338 A | 12/1994 |
| JP | 11281501 | 10/1999 |
| JP | 2002131224 | 5/2002 |
| WO | 2012128184 A1 | 9/2012 |

OTHER PUBLICATIONS

Kishii, "Surface stress meters utilizing the optical waveguide effect of chemically tempered glasses", Optics and Lasers in Engineering, vol. 4, pp. 25-38 (1983).

McRae et al; "The measurement of compression stress in eggshells"; Journal of Agricultrual Engineering Research, vol. 14, No. 1, Mar. 1, 1969.

Notification of Transmittal of the International Search Report and the Written Opinoin of the International Searching Authority; International Application No. PCT/US2014/053069; dated Dec. 9, 2014; 16 Pages.

Pelletier et al; "Optical characterization of thin films by guided waves", Applied Optics 28, p. 2918 (1989).

Tien et al; "Theory of prism-film coupler and thin film light guides", Journ. Opt. Soc. Am. 60, p. 1325 (1970).

Ulrich et al; "Measurement of thin film parameters with a prism coupler", Applied Optics 12, p. 2901 (1973).

Agan et al; "Stress effects in prism coupling measurements of thin polymer films"; App. Phys. A 80, 341-345 2005.

Brandenburg; "Stress in ion-exchanged glass waveguides"; Journal of Lightwave Technology, vol. LT4, No. 10, Oct. 1986.

Chiang et al; "Refractive-Index Profiling of Buried Planar Waveguides by an Inverse Wentzel-Kramer-Brillouin Method"; Journal of Lightwave Technology, IEEE, vol. 26, No. 11, Jun. 1, 2008 pp. 1367-1373.

Chiang et al; "Refractive-Index Profiling of Graded-Index Planar Waveguides From Effective Indexes Measured With Different External Refractive Indexes"; Journal of Lightwave Technology, IEEE, vol. 18, No. 10, Oct. 1, 2000 p. 1414 and 1416.

International Search Report and Written Opinion of the International Searching Authority; PCT/US2014/062370; dated Feb. 9, 2015.

Metricon 2010 manual, Metricon corporation.

Pitt et al; "Lightguiding in Langmuir-Blodgett Films"; Thin Solid Films, vol. 68, No. 1 May 1, 1980 p. 114.

Rau et al; "Prism coupled Terahertz waveguide sensor"; Applied Physics Letters, 86, 211119 (2005).

Surface Stress Meter FSM-60 Manual, Orihara Industrial Co.

Surface Stress Meter FSM-6000 LE Standard/Premium, Nov. 2015, URL: http://www.luceo.co.jp/en/catalog/up_img/1410507041-434950.pdf.

Tien, "Light waves in thin films and integrated optics", Applied Optics 10, p. 2395 (1971).

Ulrich; "Theroy of the prism-film coupler by plane-wave analysis"; Journal of the Optical Society of America; vol. 60, No. 10, 1970, pp. 1337-1350.

Zernike et al,; "Improved Version of the Evanescent-Wave Coupler", IEEE Journal of Quantum Electronics, Sep. 1970, pp. 577-578.

English Translation of JP2016537839 Office Action dated Jul. 3, 2018; 3 pages; Japanese Patent Office.

* cited by examiner

PRISM-COUPLING SYSTEMS AND METHODS FOR CHARACTERIZING CURVED PARTS

FIELD

The present disclosure relates to measuring stress in parts, and in particular relates to prism-coupling systems and methods for optically characterizing curved parts.

BACKGROUND

Chemically strengthened glass parts have become important for a variety of applications, including resilient, shatter-resistant and scratch-resistant, touch-enabled, protective flat cover windows for smart phones and tablets. These glass parts are thinner and lighter than thermally tempered glass yet tougher due to the high surface compression (for example, on the order of $8 \times 10^8$ Pa) achievable through an ion-exchange process.

The quick adoption, continuous improvement and dramatic market growth of such flat-glass products were boosted by the availability of quick nondestructive techniques for measuring the two major parameters of the stress profile: the surface compressive stress (CS) and depth of layer (DOL). Such measurements can be made using a commercially available high-resolution prism-coupling system, such as the FSM-6000LE made by Orihara Industrial Co., Ltd and sold by Luceo, both of Japan. The third critical parameter, the center tension (CT), may be inferred by invoking a force balance requirement between the compressive and tensile forces.

A prism-coupling system captures angular coupling spectra ("mode spectra") of transverse-electric (TE) and transverse-magnetic (TM) optical propagation modes of the ion-exchanged region. The stress is extracted from the difference between the two spectra by using the stress-optic coefficient (SOC). Due to the small SOC (~$3 \times 10^6$ RIU/MPa, wherein RIU stands for refractive index units), the stress-induced part of the refractive index represents a small difference between two much larger index numbers. Consequently, the magnitude and shape of the stress profile are strongly affected by small errors in the recovered TE and TM profiles. To minimize such errors, high-resolution capture of the TE and TM mode spectra is necessary.

The excellent strength properties of chemically strengthened glass parts make them desirable replacements for existing curved glass parts, such as test tubes, and for non-flat external glass or plastic parts of personal electronic devices. However, quick nondestructive measurement of the TE and TM mode spectra on such curved parts for the purpose of measuring one or more characteristics, such as the stress profile or some of its critical parameters, has proven problematic.

SUMMARY

An aspect of the disclosure is a method for determining at least one characteristic of a curved part having a curved outer surface. The method includes interfacing a coupling surface of a coupling prism to the curved outer surface to define a coupling interface. The method also includes directing measurement light through the coupling prism and to the interface, wherein the measurement light has a width of 3 mm or less. The method further includes digitally capturing TE and TM mode spectra reflected from the interface. The method also includes processing the TE and TM mode spectra to determine the at least one characteristic of the curved part. In an example, the at least one characteristic is selected from the group of characteristics comprising: surface stress, stress profile, compressive stress, depth of layer, refractive index profile, and birefringence.

Another aspect of the disclosure is a method for determining at least one characteristic of a curved part having a curved outer surface. The method includes: directing focused measurement light to a coupling-prism assembly having a coupling prism interfaced with the outer surface of the curved part to define a coupling interface, wherein the curved outer surface is defined by a radius $R1 \geq 0.5$ mm and a radius $R2 \geq 20$ m; reflecting the measurement light from the coupling interface while restricting the measurement light to have a width of 3 mm or less prior to said reflecting; detecting the reflected measurement light to obtain TE and TM mode spectra; and processing the TE and TM mode spectra to determine the at least one characteristic of the curved part.

Another aspect of the disclosure is a prism-coupling system for determining at least one characteristic of a curved part having a curved outer surface. The system includes: a light-source system that generates measurement light; a coupling-prism assembly having a coupling prism with input and output surfaces and a coupling surface that interfaces with the curved outer surface to define a coupling interface, wherein the coupling-prism assembly comprises means for defining a width of the measurement light to be 3 mm or less; a detector system arranged to receive measurement light reflected from the interface and that exits the output surface to digitally capture TE and TM mode spectra; and a controller that processes the TE and TM mode spectra to determine the at least one characteristic of the curved part.

Additional features and advantages are set forth in the Detailed Description that follows and in part will be readily apparent to those skilled in the art from the description or recognized by practicing the embodiments as described in the written description and claims thereof, as well as the appended drawings. It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding and are incorporated into and constitute a part of this specification. The drawings illustrate one or more embodiment(s) and together with the Detailed Description serve to explain the principles and operation of the various embodiments. As such, the disclosure will become more fully understood from the following Detailed Description, taken in conjunction with the accompanying Figures, in which.

Any coordinates or axes shown in the Figures are for the sake of reference and are not intended to be limiting as to direction or orientation. In addition, references to directions such as "vertical" and "horizontal" are used for ease of discussion with respect to select features in a given Figure and are not intended as limiting as to direction or orientation.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this Detailed Description.

The entire disclosure of any publication or patent document mentioned herein is incorporated by reference, including U.S. patent application Ser. No. 13/463,322 and 61/706,891.

Curved Part

Figure 1A:
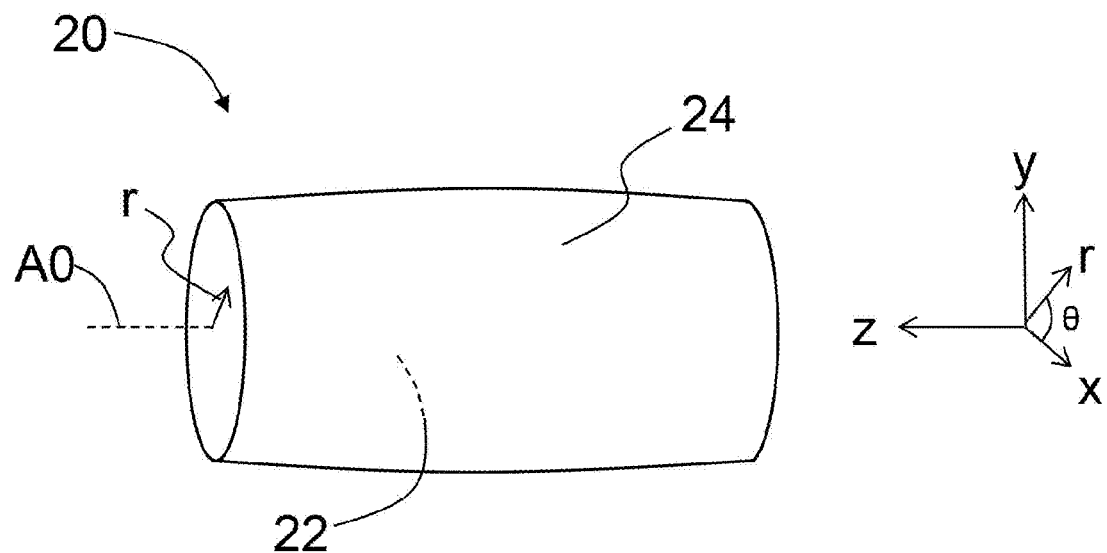
FIG. 1A is an isometric view of an example curved part.
Figure 1B:
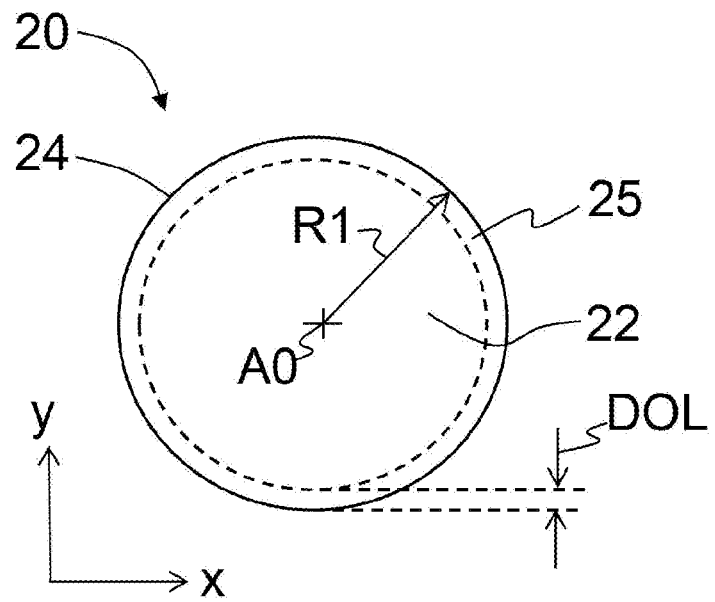
FIG. 1B is a cross-sectional view of the curved part of FIG. 1A as taken in the x-y plane and showing a first radius of curvature (R1) and an ion-exchange region that has a depth of layer (DOL)
Figure 1C:
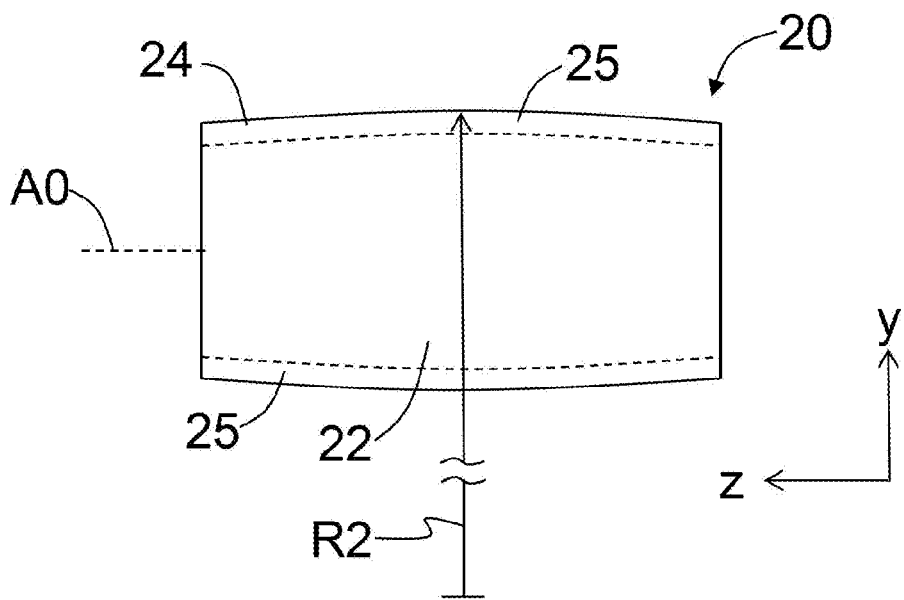
FIG. 1C is a cross-sectional view of the curved part of FIG. 1A as taken in the y-z plane and showing a second radius of curvature (R2)

FIG. 1A is an isometric view of an example curved part 20, and FIG. 1B is a cross-sectional view of the curved part taken in the x-y plane. The curved part 20 has a body 22 and a curved outer surface 24. In an example, curved part 20 is made of glass and has a base (or bulk) refractive index $n_s$. FIG. 1A shows Cartesian coordinates, along with polar coordinates (r,θ). FIG. 1C is a cross-sectional view of curved part 20 taken in the y-z plane. In an example, curved part 20 may be a rod, or it may be a tube having a hollow interior portion. In an example, curved part 20 has a central axis A0.

Figure 1D:
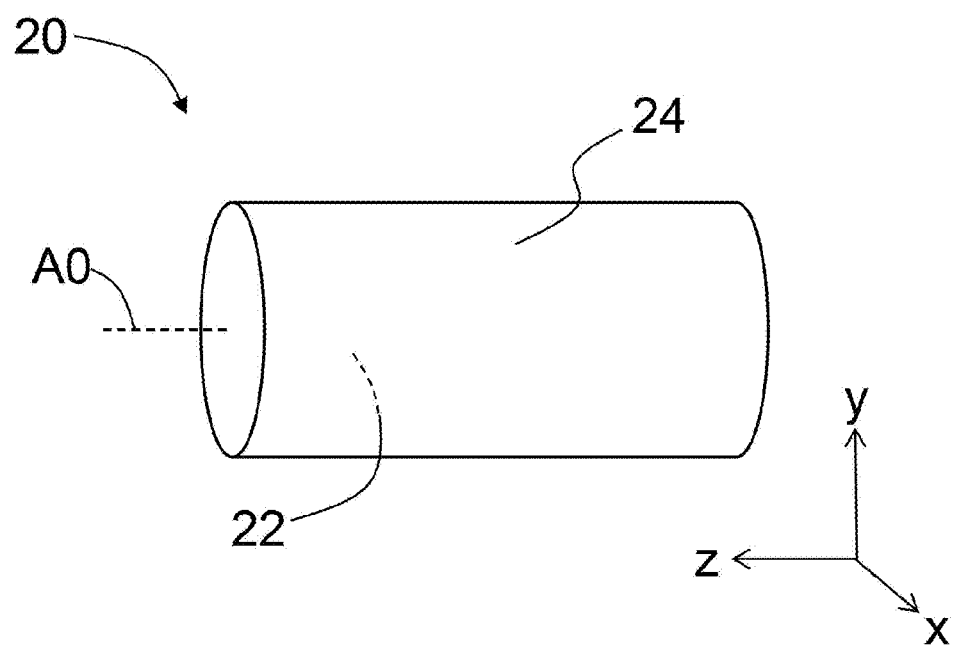
FIG. 1D is similar to FIG. 1A and illustrates an example of a perfectly cylindrical part for which the second radius of curvature is infinite.

The outer surface 24 of curved part 20 has a first radius of curvature R1 in the x-y plane and a second radius of curvature R2 in the y-z plane. In an example, first radius of curvature R1 can be relatively small while second radius of curvature R2 is relatively large. In an example, first radius of curvature R1≥0.5 mm, while second radius of curvature R2≥20 m. In the example of curved part 20 as shown in FIG. 1D, second radius of curvature R2=∞ so that FIG. 1D is a cylinder. The curvature can be outward as shown by way of example, or can also be inward. First and second radii R1 and R2 are used herein to describe either inward or outward curvature.

In an example where second radius of curvature R2≠∞, the second radius of curvature R2 is sufficiently large as compared to first radius of curvature R1 for curved part 20 to be substantially cylindrical or conical in a portion of its surface that is to be used for making mode spectra measurements. The second radius of curvature R2 is dictated in part by the size of the coupling prism 40 (introduced and discussed below in connection with FIG. 2). In an example, the second radius of curvature R2 is many times larger than the length of the coupling prism 40 in the z-direction.

Also in an example, first radius of curvature R1 need not be constant, as in conical surfaces. Curved part 20 may also have a complex surface, such as a combination of flat and curved portions, and simple curved parts are shown in the Figures for ease of illustration.

In an example, curved part 20 is made of glass that has undergone an ion-exchange process whereby at least one type of ion has been exchanged through outer surface 24 and into body 22. The ion-exchange process defines an ion-exchanged region 25 (FIG. 1B and FIG. 1C) that has a refractive index profile n(r) that may be different for s-polarized (transverse electric, TE) light than for p-polarized (transverse magnetic, TM) light, which is polarized parallel to its plane of incidence.

The (radial) depth of ion-exchanged region 25 as measured directly inward from (i.e., in a direction perpendicular to) outer surface 24 is called the "depth of layer" or DOL. An example range for the DOL is from 5 to 150 microns. The DOL is most often smaller than half the thickness of the sample, including cases where the sample is a hollow tube and the sample thickness is represented by the thickness of the tube wall.

The ion-exchange process that forms ion-exchanged region 25 in curved part 20 can give rise to birefringence B at and near outer surface 24 of curved part 20. This birefringence B can be used to calculate the stress (e.g., compressive stress CS) at (and near) outer surface 24, and/or the stress profile S(r), using known techniques. The stress profile is related to birefringence B via S(r)=B(r)/SOC, where SOC is the stress-optic coefficient and B(r)=[$n_{TM}$(r)−$n_{TE}$(r)].

The spectra of optical modes (i.e., the TE and TM mode spectra) of curved part 20 are not properly imaged and captured using existing prism-coupling-based optical instruments that are used to measure flat parts. When curved part 20 is in contact with a prior-art coupling prism, the images of the optical angular spectrum (i.e., the TE, TM mode spectra) become blurred and sometimes also distorted. This makes automatically identifying the effective indices of the guided optical modes problematic, which in turn makes an accurate determination of one or more characteristics (e.g., the stress profile S(r)) that rely on such measurements problematic.

In an experiment, a conventional prism-coupling system (e.g., the FSM-6000LE prism-coupling instrument made by Orihara Industrial Co., Ltd., of Tokyo, Japan) was used to measure stress in a cylindrical glass sample having a first radius of curvature R1=8.5 mm and R2=∞. The dark lines corresponding to coupling into TE and TM modes guided in a near-surface waveguide region defined by ion-exchanged region 25 could be observed only if the sample was precisely aligned such that the axis of the measured cylinder, and the contact line between the cylinder and the coupling surface of the prism, lay in a plane orthogonal to the prism facets used for light input and output.

In addition, even with optimum alignment, the dark lines of the mode spectra were very broad and very faint in comparison with the sharp high-contrast lines normally observed during measurements of flat glass samples with near-surface planar waveguides. Captured images of the mode spectra could not be automatically processed with the commercial FSM-6000LE system software to obtain the stress parameters due to inadequate contrast of the spectral lines. Manual detection of spectral line positions of the mode spectra images lead to significant error due to the poor contrast, as well as due to the strong dependence of the image pattern on the sample alignment.

Prism-Coupling System for Measuring Curved Parts

Figure 2:
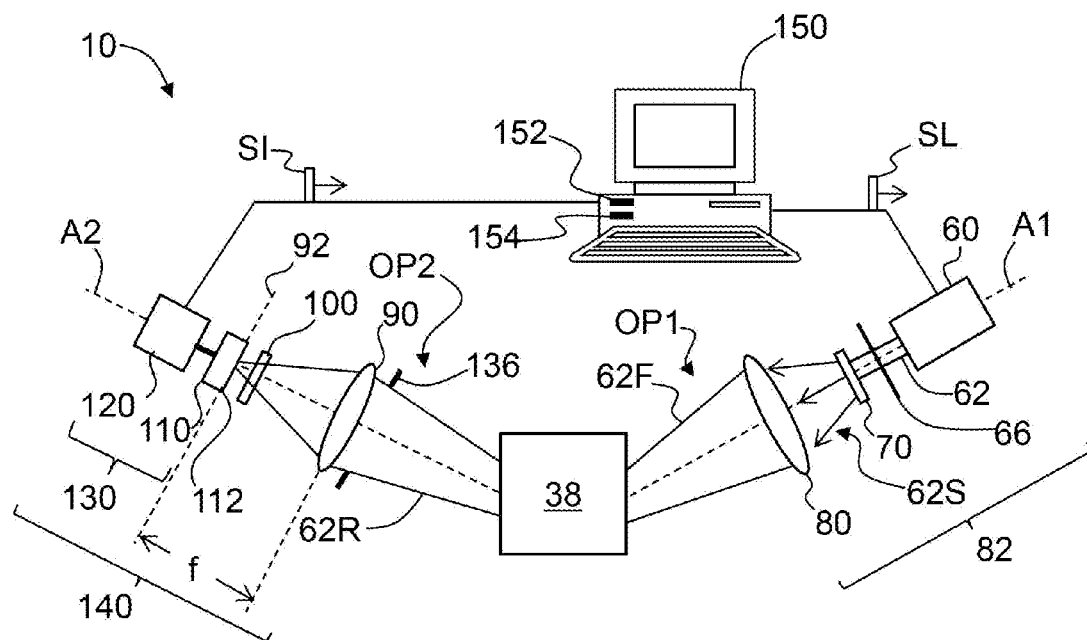
FIG. 2 is a schematic diagram of an example embodiment of a prism-coupling system that can be used to measure the mode spectra of curved parts using the methods disclosed herein.

FIG. 2 is a schematic diagram of an example prism-coupling system ("system") 10 suitable for use in measuring the mode spectra of curved parts such as curved part 20. The system 10 includes a coupling-prism assembly 38, discussed in greater detail below. The system 10 includes optical axes A1 and A2 that intersect at coupling-prism assembly 38.

The system 10 includes, in order along axis A1, a light source 60 that emits measurement light 62 of wavelength λ, an optional optical filter 66 that may be alternatively included in the detector path on axis A2, an optional light-scattering element 70, and an optional focusing optical system 80 that forms focused (measurement) light (light beam) 62F, as explained below. Thus, in an example of system 10, there are no optical elements between light source 60 and coupling-prism assembly 38. Light source 60, optional filter 66, optional light-scattering element 70, and optional focusing optical system 80 constitute an example light source system 82 that generates focused measurement light 62F.

The system 10 also includes, in order along axis A2 from coupling-prism assembly 38, a collecting optical system 90 that has a focal plane 92 and a focal length f and that receives reflected light 62R as explained below, a TM/TE polarizer 100 with TM and TE polarizing sections 100TE and 100TM, and a photodetector system 130. The axis A1 defines the center of an optical path OP1 between light source 60 and coupling-prism assembly 38. The axis A2 defines the center of an optical path OP2 between coupling-prism assembly 38 and photodetector system 130. Collecting optical system 90, TM/TE polarizer 100, and photodetector system 130 constitute an example detection system 140.

Detection system 140 can also include aperture 136 on either side of collection optical system 90. Aperture 136 can be configured to reduce the amount of "overcoupled" light that is detected by photodetector system 130. Here, "overcoupled light" is reflected light 62R that comes from coupling prism 40 but that does not represent the actual TM and TE mode spectra, as explained in greater detail below.

Figure 3A:
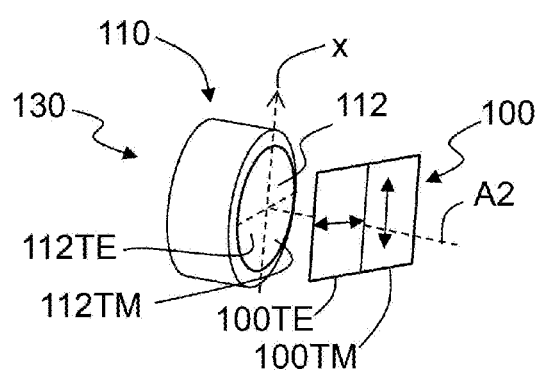
FIG. 3A is an elevated view of the example photodetector system of the prism-coupling system of FIG. 2, showing a TE/TM polarizer and a detector.

FIG. 3A is a close-up view of photodetector system 130. In an example, photodetector system 130 includes a detector 110 (e.g., CCD camera), which may for wavelengths longer than 1100 nm may be replaced with an IR analog detector and a frame grabber 120 (see FIG. 2). In other embodiments discussed below, detector 100 comprises a CMOS detector, or one or two linear photodetectors (i.e., a line of integrated photodiodes or photo-sensing elements). Detector 110 may also comprise one or more microbolometers, a microbolometer camera, one or more InGaAs-based photodetectors or an InGaAs camera.

Detector 110 includes a photosensitive surface 112. The photosensitive surface 112 resides substantially in focal plane 92 of collecting optical system 90, with the photosensitive surface being generally perpendicular to axis A2. This serves to convert the angular distribution of reflected light 62R exiting coupling-prism assembly 38 to a transverse spatial distribution of light at the sensor plane of detector 110.

Splitting photosensitive surface 112 into TE and TM sections 112TE and 112TM allows for the simultaneous recording by detector 110 of digital images of the angular reflection spectra (containing the mode spectra) for the TE and TM polarizations of reflected light 62R. This simultaneous detection eliminates a source of measurement noise that could arise were the TE and TM measurements to be made at different times, given that system parameters may drift with time.

Figure 3B:
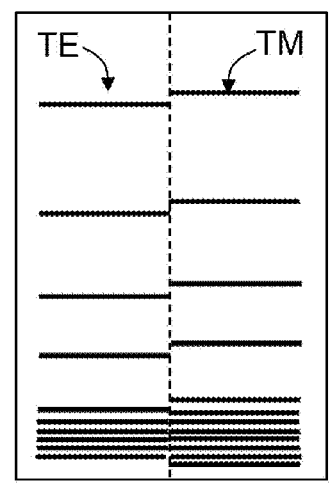
FIG. 3B is a schematic diagram of the TE and TM mode spectra as captured by the photodetector system of FIG. 3A using the prism coupling system of FIG. 2.

FIG. 3B is a schematic diagram of the TE and TM mode spectra as captured by the example photodetector system of FIG. 3A. The TE and TM mode spectra are shown as having a high contrast for the sake of illustration.

Example light sources 60 include visible or infrared lasers, visible or infrared light-emitting diodes, visible or infrared amplified-spontaneous-emission (ASE) sources, visible or infrared super-luminescent-diode (SLD) sources, and broader-bandwidth sources such as hot-filament lamps and quartz lamps combined with proper means of narrowing the optical spectrum including wavelength-selective filters or diffraction gratings. Example operating wavelengths λ of light 62 generated by light source 60 include visible wavelengths such as 405 nm, 488 nm, 590 nm, 633 nm, and infrared wavelengths, such as (nominally) 820 nm, 940 nm, 1,060 nm, 1,550 nm, 1,613 nm, 1,900 nm or 2,200 nm.

Any light source 60 of the enumerated above types with a main wavelength range from 400 nm to 2,200 nm and adequate brightness can be configured to enable the measurement methods disclosed herein, when combined with a photodetector system 130 that is sensitive at the wavelength λ of the light source, and in some cases when appropriate narrowing of the optical spectrum is included. The required brightness depends on the sensitivity of detector 110 and the noise equivalent power, including fundamental detector noise, and external electrical noise or background light.

The system 10 includes a controller 150 that may be configured to control the operation of the system. The controller 150 is also configured to receive and process (image) signals SI from photodetector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown). In one embodiment, the TE and TM spectra may be collected sequentially, where the TE/TM polarizer 100 may contain a single section passing a single polarization only. In this case, the polarizer may be rotated between two orientations having 90° difference in the polarization direction, and the controller 150 may control the switching of the polarizer between the two orientations, and the synchronization of that switching with the sequential collection of the TE and the TM spectra.

In an example, controller 150 comprises a computer and includes a reading device, for example, a floppy disk drive, a CD-ROM drive, a DVD drive, a magnetic optical disk (MOD) device (not shown) or any other digital device including a network-connecting device, such as an Ethernet device (not shown), for reading instructions and/or data from a computer-readable medium, such as a floppy disk, a CD-ROM, a DVD, a MOD, a flash drive or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the aforementioned signal processing of image signals SI to arrive at a measurement of at least one characteristic of the measured curved part, such as a surface stress, a stress profile, a compressive stress, a depth of layer, a refractive index profile, and a birefringence.

As used herein, the term "computer" is not limited to just those integrated circuits referred to in the art as computers but broadly refers to computers, processors, microcontrollers, microcomputers, programmable logic controllers, application-specific integrated circuits and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer, e.g., by the processor 152.

In operation, the code and possibly the associated data records are stored within a general-purpose computer platform, within processor 152 and/or in memory 154. At other times, however, the software may be stored at other locations and/or transported for loading into the appropriate general-purpose computer systems. The embodiments discussed herein involve one or more software products in the form of one or more modules of code carried by at least one machine-readable medium. Execution of such code by processor 152 of computer 150 enables the platform to implement the catalog and/or software downloading functions in essentially the manner performed in the embodiments discussed and illustrated herein.

The computer 150 and/or processor 152 may each employ a computer-readable medium or machine-readable medium (e.g., memory 154), which refers to any medium that participates in providing instructions to the processor for execution, including, for example, determining an amount of surface birefringence/stress or the stress profile S(x) of curved part 20. The memory 154 constitutes a computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; and a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

The system 10 may be a modified version of the aforementioned commercial prism-coupling instrument, such as the FSM-6000LE prism-coupling instrument made and sold by Orihara Industrial Co., Ltd., of Tokyo, Japan.

Coupling-Prism Assembly

Figure 4A:
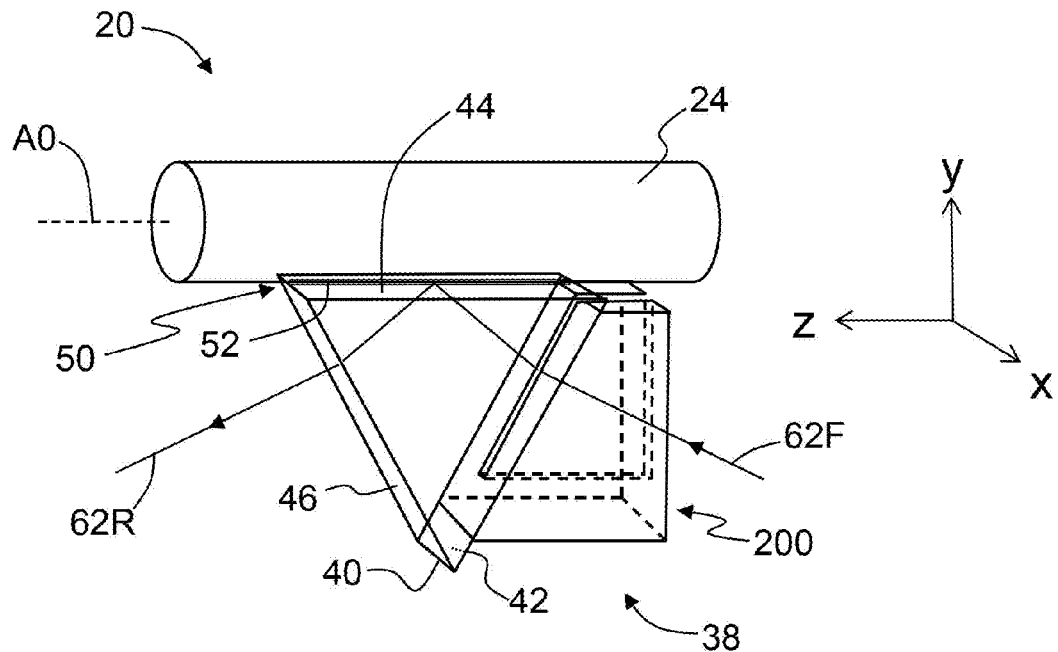
FIG. 4A is a close-up view of an example coupling-prism assembly of the prism-coupling system of FIG. 2 that shows a coupling prism and a light-restricting member that is arranged adjacent the coupling-prism input surface and that has a narrow slot that restricts the light available on the prism-coupling surface to a narrow spatial region that is not constrained in the z-direction.
Figure 4B:
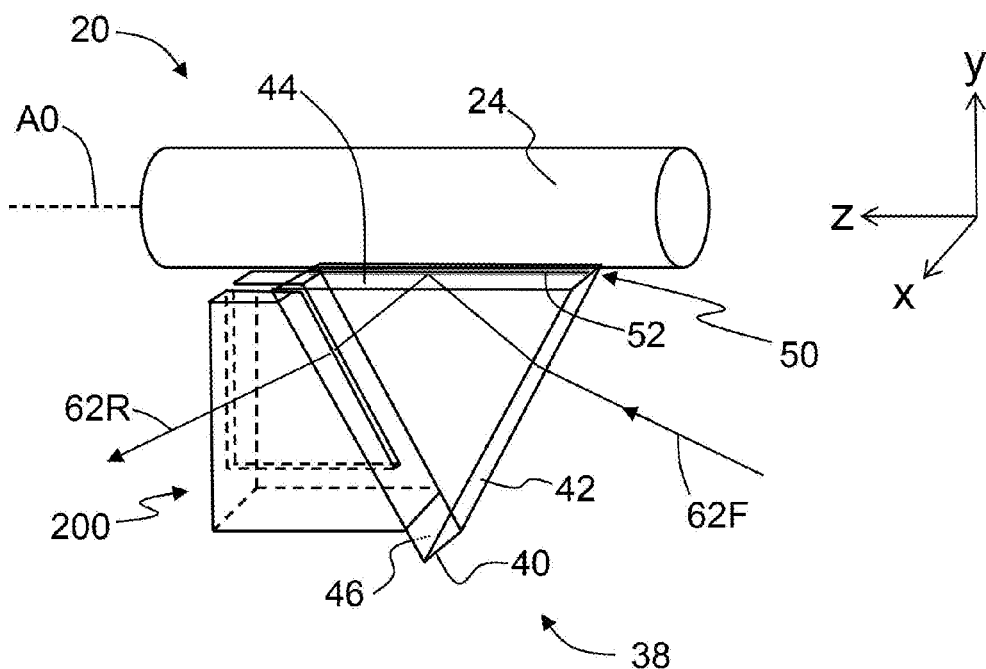
FIG. 4B is similar to FIG. 4A and shows the light restricting member arranged adjacent the output surface rather than the input surface.
Figure 4C:
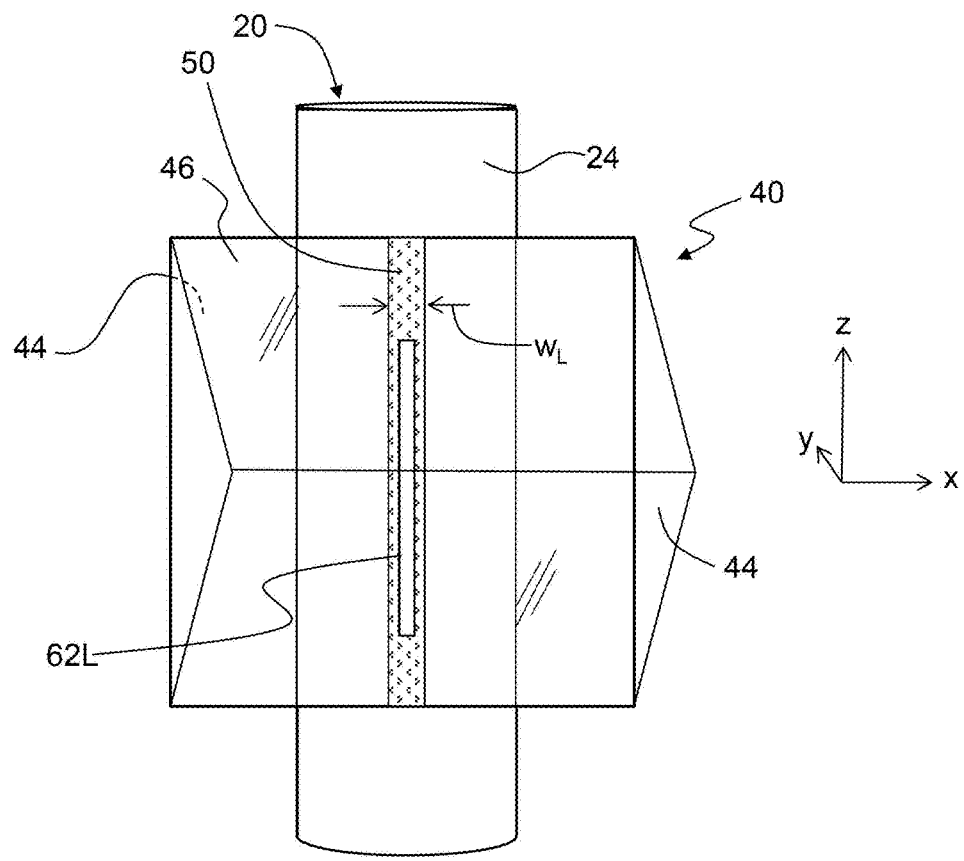
FIG. 4C is a top-down view of coupling prism as arranged in FIG. 4A or FIG. 4B and that shows a long and narrow region of optical contact that defines the part-prism coupling interface, and also shows the illumination region formed by the measurement light beam.
Figure 5A:
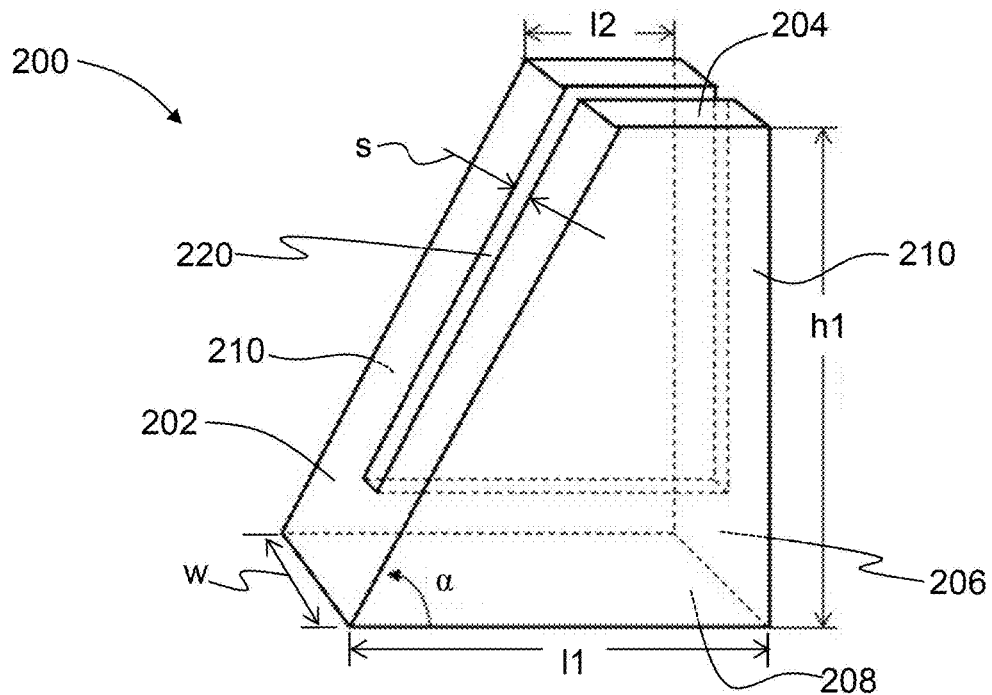
FIGS. 5A and 5B are elevated and front-on views of the example light-restricting member of FIGS. 4A and 4B.
Figure 5B:
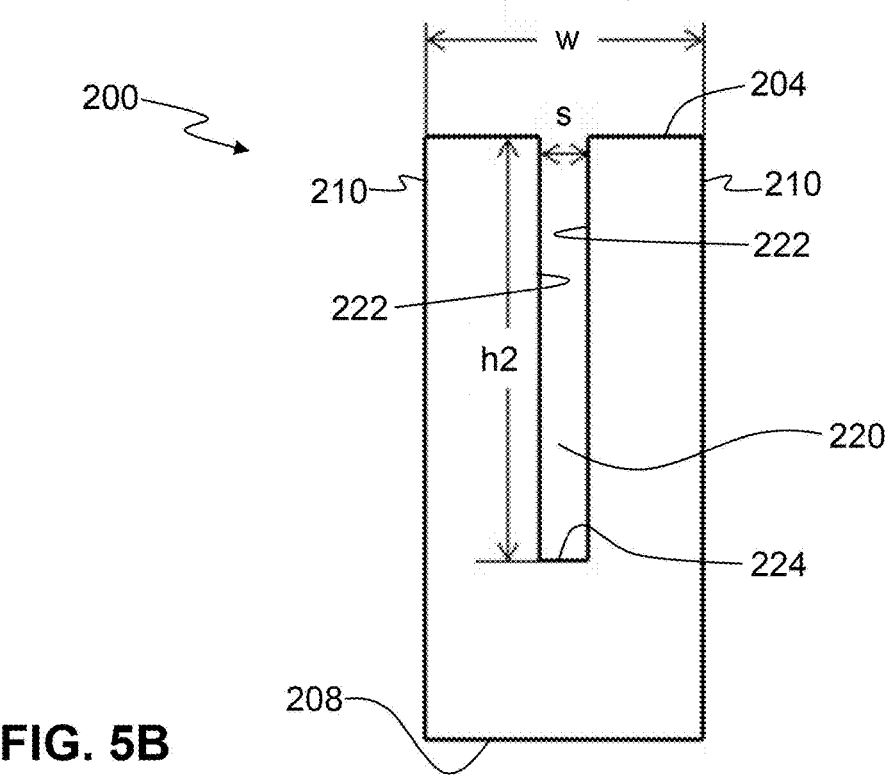

FIGS. 4A and 4B are side views of example configurations for coupling-prism assembly 38, shown interfaced with an example curved part 20 and including an example light-restricting member 200. FIGS. 5A and 5B are elevated and front-on views of the example light-restricting member 200 of FIGS. 4A and 4B;

The coupling-prism assembly 38 includes a coupling prism 40 that has an input surface 42, a coupling surface 44 and an output surface 46. The coupling prism 40 has a refractive index $n_p > n_s$. The coupling prism 40 is interfaced with curved part 20 by bringing coupling-prism coupling surface 44 and a portion of curved outer surface 24 into optical contact. FIG. 4C is a top-down view of the coupling prism 40 of FIG. 4A and FIG. 4B and shows a long and narrow region of optical contact between part outer surface 24 and coupling surface 44 that defines a long and narrow part-prism coupling interface ("interface") 50.

Figure 4D:
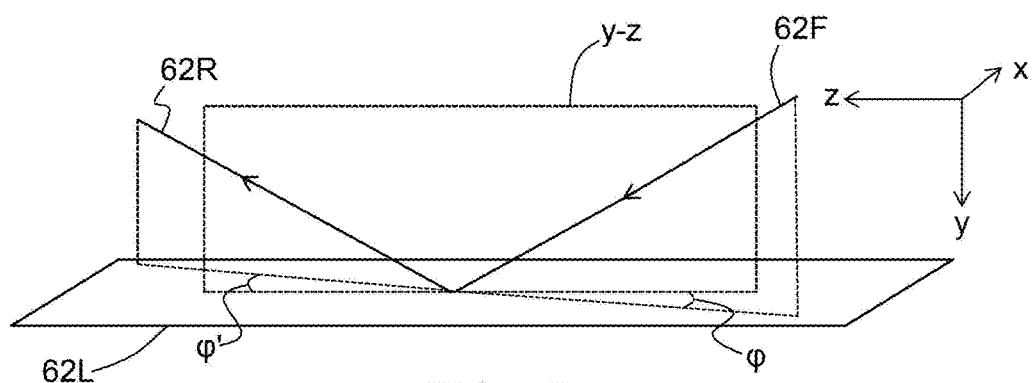
FIG. 4D is an elevated view of illumination region of FIG. 4C and shows the y-z plane and example out-of-plane light beams that have an out-of-plane angle φ as projected onto the x-z plane.

FIG. 4C also shows an illumination region 62L formed by measurement light beam 62F. In an example, illumination region 62L and interface 50 are elongate and are substantially aligned along their respective long axes. FIG. 4D is an elevated view of illumination region 62L showing the y-z plane and out-of-plane light beams 62F and 62R. The out-of-plane angle is denoted φ. Illumination region 62L has a width in the x-direction of $w_L$. The example illumination region 62L is shown as having a constant width $w_L$, but $w_L$ can also vary with the length of the illumination region.

In an example, a thin layer of interfacing fluid 52 of refractive index $n_f$ is used to facilitate optical coupling between coupling prism 40 and curved part 20 and constitutes part of interface 50. In an example, $n_p \geq n_f > n_s$. An example value for $n_f = 1.64$. In another example, the interfacing fluid index $n_f = n_p \pm 0.02$. In a specific related example, the prism index may be $n_p = 1.72$.

The coupling-prism assembly 38 of FIGS. 4A and 4B include the aforementioned example light-restricting member 200, which is adapted to interface with coupling prism 40 at either input surface 42 (FIG. 4A) or output surface 46 (FIG. 4B). The example light-restricting member 200 is in the form of a truncated right-angle prism that either is made of an opaque material or has an opaque coating. The light-restricting member 200 has an angled front surface 202, a truncated top surface 204, a back surface 206, a bottom surface 208, and parallel sides 210. The light-restricting member 200 has a height h1, a base length l1 at bottom surface 208, a top length l2 at truncated top surface 204, and a width w, as shown. The bottom surface 208 and angled front surface 202 define an angle α.

The light-restricting member 200 includes a central slot 220 that is open at surfaces 202, 204 and 206. The central slot 220 has inner surfaces 222 and a bottom 224 that resides above bottom surface 208 and so has a height h2<h1. In one example, inner surfaces 222 are parallel to sides 210 and so define a slot 220 having a uniform width s. In other examples, central slot 220 can be configured to have a width s that varies along its length, e.g., linearly, or in a curved manner. The slot width s can be selected to define various degrees of light restriction. In an example, inner surfaces 222 of slot 220 have a light-absorbing coating, e.g., are painted dark, are oxidized or anodized, etc., to reduce specular and diffuse reflections.

Example values of the dimensions for the example light-restricting member 200 are set forth in Table 1, below:

TABLE 1

| Dimension | Value |
| --- | --- |
| l1 | 0.695 inches |
| | (17.65 mm) |
| l2 | 0.25 inches |
| | (6.35 mm) |
| h1 | 0.77 inches |
| | (19.55 mm) |
| h2 | 0.62 inches |
| | (15.75 mm) |
| w | 0.195 inches |
| | (4.95 mm) |
| s | 0.01 to 0.04 inches |
| | (0.25 mm to 1 mm) |
| α | ~60 degrees |

In an example, one or two light-restricting members 200 are arranged relative to coupling prism 40 to restrict the illumination region 62L to long and narrow interface 50 and to restrict light beams 62F and 62F to have a narrow range of angle φ outside of the y-z plane (FIG. 4D). In an example, the size of illumination region 62L and the range of angle φ are defined by the width s of central slot 220. In an example, the one or two light-restricting members are arranged immediately adjacent the input and/or output surfaces 42 and 46 of coupling prism 40. In another example, the one or two light restricting members are spaced apart from the input and/or output surfaces 42 and 46 of coupling prism 40.

The mode spectra image captured by photodetector system 130 (see, e.g., FIG. 3B) represents the angular spectrum of reflection from interface 50 for TM waves. Bright areas on the image correspond to high reflection, and dark lines correspond to coupling of measurement light 62F into guided or sometimes well-defined leaky modes. Extended dark regions are usually associated with coupling to leaky modes and radiation modes into the substrate. Experiments performed using light-restricting member 200 in coupling-prism assembly 38 in system 10 resulted in a several-fold increase in contrast and sharpness of the TE and TM mode spectra as compared to employing the unrestricted effective illumination and collection width of 5 mm (0.197 inches) of the unrestricted prism assembly supplied with the conventional FSM-6000LE instrument.

Experiments on an example curved part 20 included capturing mode spectra images for a sample with first radius of curvature R1=8.5 mm and a DOL of 23 microns. The mode spectra images showed observable improvement in contrast for slot widths s<3 mm and even greater improvement for slot widths s<1.5 mm, as compared to the mode spectra contrast for the standard collection width of 5 mm. From these observations and dimensions of the light restricting member 200 described above and those of coupling prism 40, an improvement in the mode spectra contrast may be obtained when prism coupling surface 44 is illuminated with focused light beam 62F that is narrowed to about 3 mm or smaller.

A contrast improvement during measurements of curved parts may also be observed when light beams 62F incident on prism assembly 38 have projections in the plane of the prism coupling surface 44 that are restricted to subtend angles smaller than about 10° with respect to the symmetry line of the illuminated strip, which is designed to coincide with the contact line between the curved portion of the curved part 20 and prism coupling surface 44.

The improvement in the contrast of the mode spectra is due in part to rejecting light that does not interact with the sample. This light rejection is already substantial when the slot width s in the described experiment is in the range from 1.5 mm to 3 mm. For even smaller slot widths s, there can be even greater improvement. The contrast improvement is also due in part to rejecting light rays whose projections in the plane of coupling surface 44 form large angles with the sample-prism contact line that defines interface 50.

For large slot widths s, these undesired light rays can be blocked by aperture 136 (see FIG. 2), or other apertures normally disposed in the detecting system 140 of system 10. Hence, the angular component of the improvement that is due to light restricting member 200 becomes more significant for slot sizes s<1.5 mm, e.g., when the light rays 62R that pass through prism assembly 38 and reach photodetector system 130 have projections in the plane of coupling surface 44 that are restricted to angles φ smaller than about 5° (see FIG. 4D). Note that in some cases the projection angle φ' of a reflected ray from beam 62R may be somewhat different than the projection angle φ of the corresponding incident ray from beam 62F, after interaction with the curved surface of the sample.

Thus any slot, a combination of slits, or combination of apertures (e.g., such as aperture 136) that may be placed near or far from coupling prism 40, and that restrict the illumination such that φ≤±10°, and in particular φ≤±5° may contribute to improving the contrast of the measured mode spectra. The angular range of φ is defined as Δφ, and in examples is limited to 20°, or in a more narrow example is limited to 10°.

Both the width $w_L$ of the illuminated region 62L and the angular range Δφ associated with the illumination region can be defined by at least two apertures of system 10. In an example as described above, the two apertures are the input and output ends of slot 220 at the front and back surfaces 202 and 206 of light restricting member 200 (see, e.g., FIG. 5A). In other examples, one of the apertures may be part of detection system 140, such as aperture 136, that serve to reduce contrast reduction due to parasitic unwanted illumination and also effects of "over coupling" where some of the focused light 62F resonantly couples into and out of curved part 20 in a way that when the reflected light 62R reaches photodetector system 130, it increases the optical intensity at a location (e.g., at an angle) where a dark line should be observed.

Thus, one aperture in system 10 may be slot 220 of light restricting member 200, where another aperture is defined by a simple slit or restricted opening added to define the width of illumination region 62L. Such an aperture in a standard prism-coupling system is usually too large to effectively help to improve the mode spectra contrast for measuring curved parts. For radii of curvature R1<10 mm, in an example, the two apertures are defined by slot 220 at the front and back ends 202 and 206 of light restricting member 200.

When measuring curved part 20 in system 10, reflected light 62R is sent toward photodetector system 130 from the entire coupling surface of the prism. Of that signal, only a small fraction of reflected light 62R is reflected from the long and narrow interface 50. The measurement light 62F that interacts with areas of curved part 20 that are substantially separated from coupling prism 40 and that curve progressively away from the coupling prism is either spread over or deflected outside of the field of view of photodetector system 130. This has been identified as one cause for the dramatic contrast degradation in the mode spectra when curved parts 20 are measured using a conventional prism-coupling measurement system.

More Coupling Prism Assembly Examples

Figure 6A:
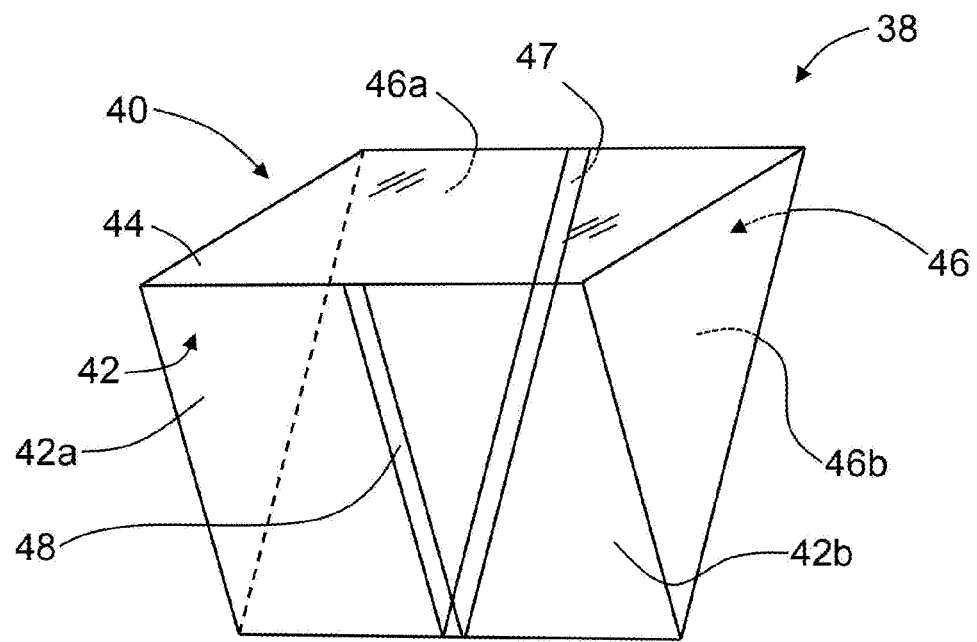
FIG. 6A is an elevated view of an example coupling prism wherein the input and output surfaces include opaque regions that define a slit opening.

FIG. 6A is an elevated view of an example coupling-prism assembly 38 wherein the input and output surfaces 42 and 46 of coupling prism 40 include respective opaque sections 42a, 42b and 46a, 46b that define slits 47 and 48 through which light can pass. In an example, opaque sections 42a, 42b and 46a, 46b are defined by an absorbing layer formed on the opaque sections of input and output surfaces 42 and 46. The slits 47 and 48 can be defined using conventional masking techniques. In another example, opaque sections 42a, 42b and 46a, 46b can be separate sheets or films that are placed immediately adjacent (e.g., in intimate contact with or slightly spaced apart from) input and output surfaces 42 and 46. The slits 47 and 48 serve the same purpose as central slot 220 of light-restricting member 200 to define the width of the measurement light 62 and so can also be referred to as a "slot" for uniformity of terminology.

In the embodiment of FIG. 6A, the slot is composed of the two slits 47 and 48, one near or on the input prism surface, and one near or on the output prism surface. FIG. 6A also represents another embodiment where coupling prism 40 contains three regions, where the central region 48 is transparent at the measurement wavelength, while the regions on either side of it absorb strongly at the measurement wavelength. Such a coupling prism 40 may be obtained by fusing together three prisms made of the same or similar glasses, where the two outer glasses are doped with iron or other absorbing ion, and possibly annealed in a reducing environment to enhance the absorption at the measurement wavelength.

Figure 6B:
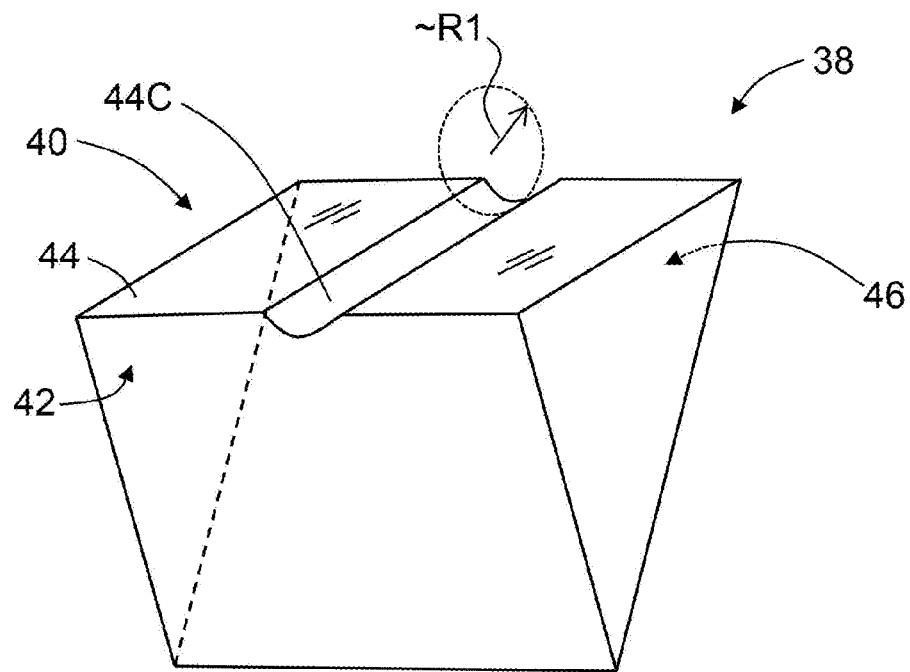
FIG. 6B is an elevated view of an example coupling prism that has a curved section on the coupling surface.

FIG. 6B is similar to FIG. 6A and shows an example coupling prism 40 wherein coupling surface 44 includes a cylindrically curved portion 44C that in an example is inwardly curved and has a radius of curvature of about R1 (i.e., ~R1). This particular coupling prism 40 can be used advantageously in coupling prism assembly 38 along with light-blocking features, such as one or more light-restricting members 200, or opaque sections 42a, 42b and/or 46a, 46b. In an example, the radius of the curved portion 44C is between about 0.5R1 and 1.5R1. In an example, interfacing fluid 52 with $n_f > n_s$ is employed, especially when the radius of the curved portion of part 20 is smaller than R1.

Figure 6C:
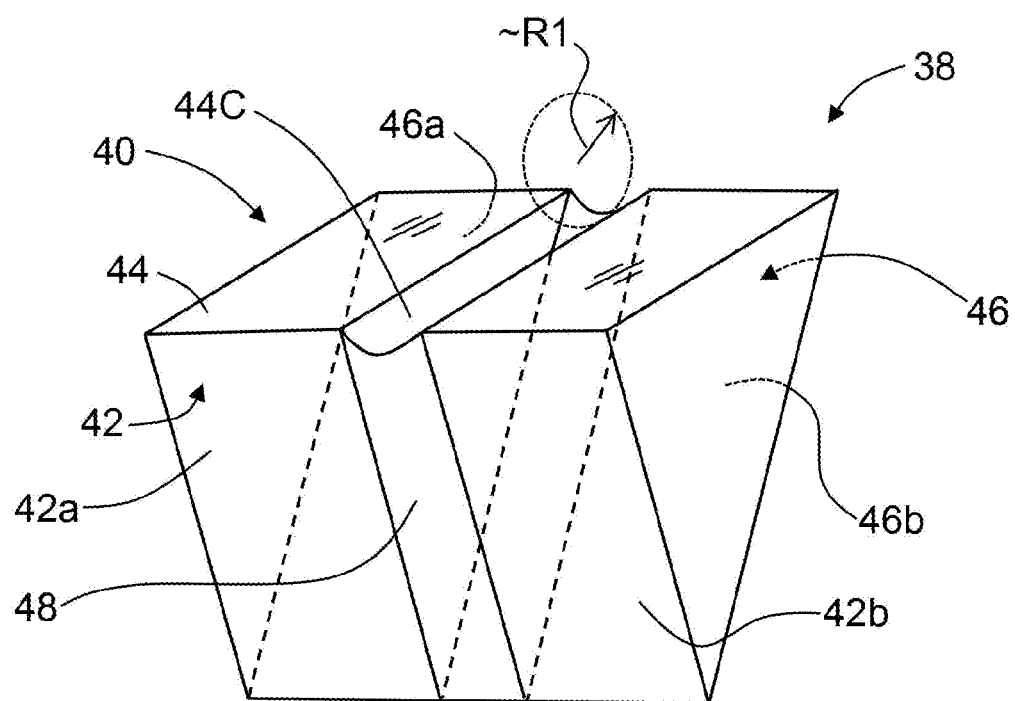
FIG. 6C is an elevated view of an example coupling prism that combines the features of the coupling prisms of FIGS. 6A and 6B.

FIG. 6C shows an example coupling prism 40 that combines the features of the coupling prisms of FIGS. 6A and 6B, so that the resulting coupling prism has both a cylindrically curved portion 44C and opaque sections 42a, 42b and 46a, 46b. In an example, cylindrically curved portion 44C has substantially the same width as the width of slit 48. In another example, the cylindrically curved portion 44C is wider than the slit 48.

Figure 7A:
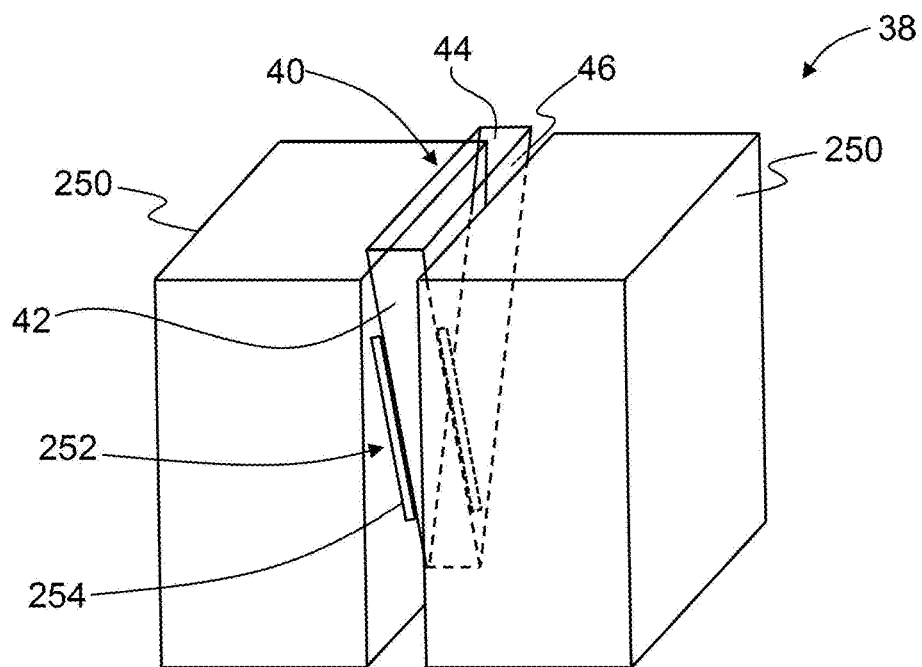
FIG. 7A is an example coupling-prism assembly that includes a thin prism supported by two opaque light-absorbing blocks.

FIG. 7A is an elevated view of another example embodiment of coupling-prism assembly 38 that includes a narrow coupling prism 40 sandwiched by two blocks 250. The blocks 250 are opaque and can be part of a unitary block of opaque material or two separate blocks. The blocks 250 therefore define a narrow slot 252 within which narrow coupling prism 40 resides. In an example, the facets of the blocks 250 that face narrow coupling prism 40 have strong light absorption at the measurement wavelength, or may be interfaced with the prism coupling using glue or other material that has strong optical absorption at the measurement wavelength.

An example narrow coupling prism 40 has a width of about 3 mm or less and in an example has a width of about 2 mm or less. The lower limit on the width of narrow coupling prism 40 is defined by adverse scattering and diffraction effects, which in an example arise for a width less than about 0.2 mm. In an example, blocks 250 can include mounting and alignment features 254 for mounting and aligning coupling prism 40 with respect to the blocks. In an example, narrow slot 252 in which coupling prism 40 resides ensures the required light restriction for good mode spectra contrast, as well as the proper alignment with respect to the rest of system 10.

Figure 7B:
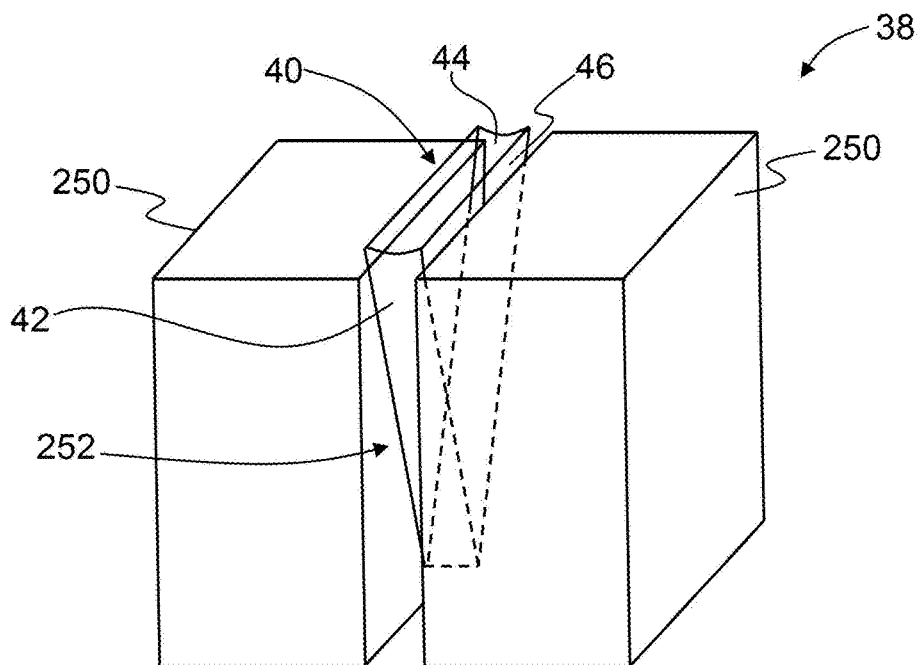
FIG. 7B is similar to FIG. 7A and shows an example wherein the coupling prism has a curved coupling surface.

FIG. 7B is similar to FIG. 7A, except that coupling surface 44 of coupling prism 40 is curved and in particular has a generally cylindrical concave curvature. In an example, the radius of curvature of curved coupling surface 44 is similar to that of first radius of curvature R1 of curved part 20 to be measured and in an example may be slightly larger. The use of concave cylindrical coupling surface 44 allows for self-alignment of curved part 20 for measurements and may significantly reduce measurement time.

Figure 7C:
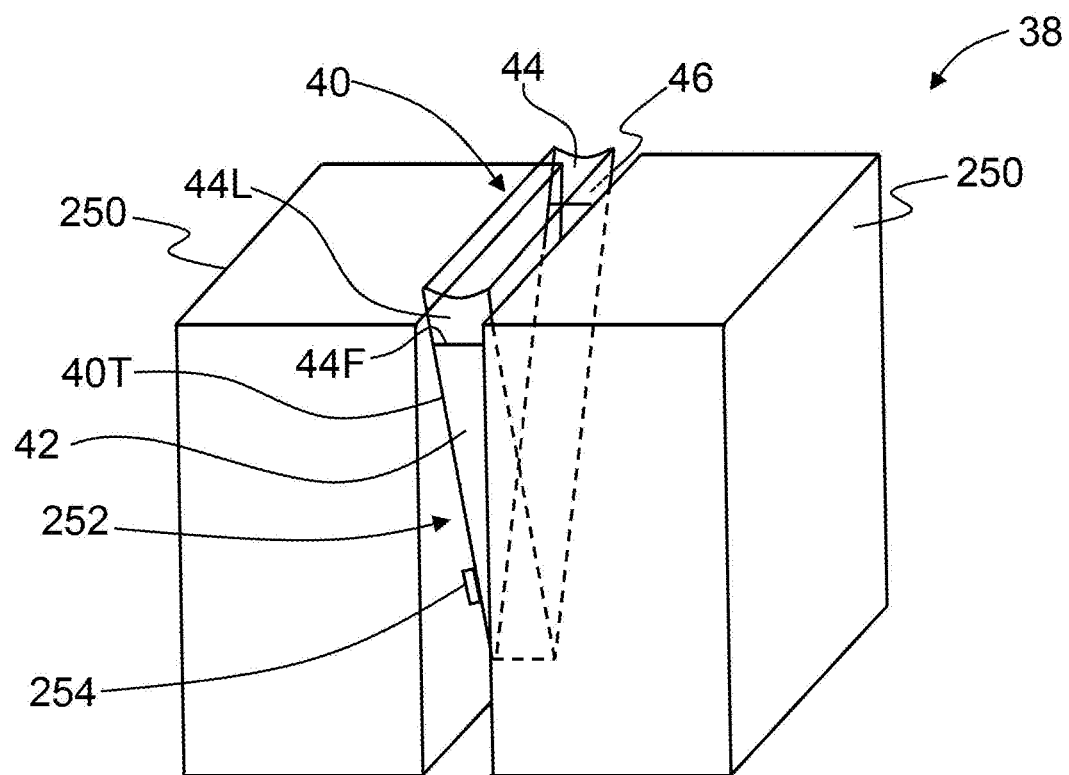
FIG. 7C is similar to FIG. 7B and shows an example wherein the coupling prism has a top section and a replaceable concave-flat cylindrical lens section that defines a curved coupling surface.

FIG. 7C is similar to FIG. 7B and illustrates an example coupling-prism assembly 38 wherein coupling prism 40 includes a thin prism section 40T with a flat base 44F and a replaceable concave-flat cylindrical lens section ("cylindrical lens") 44L that interfaces with flat base 44F and that defines a curved coupling surface 44. In an example, at least a portion of cylindrical lens 44 is held by blocks 250. In an example, thin prism section 40T is held by blocks 250 via an adhesive, an index-matching oil, a vacuum or by optical contact.

Alignment Fixture

Successful measurements of the stress in curved part 20 require mode spectra having sufficient contrast, which in turn requires that coupling prism 40 be precisely aligned relative to the curved part. In particular, coupling prism 40 needs to contact outer surface 24 of curved part 20 in a manner that matches illumination region 62L as defined by central slot 220 of light-restricting member 200 (FIG. 5A), slits 47 and 48 defined by opaque sections 42a, 42b and 46a, 46b (FIG. 6A), or narrow slot 252 defined by blocks 250 and narrow coupling prism 40 (FIG. 7A). A slight angular misalignment (<1°) results in tilting of the spectral lines (fringes), which results in measurement error. Larger angular misalignment (of just a few degrees) leads to blurring and even disappearance of the fringes.

For coupling-prism assemblies 38 that do not provide for alignment of curved part 20, an alignment fixture may be used for such alignment while allowing for fine positioning and angular alignment of the curved part to optimize the measured mode spectra contrast.

Figure 8:
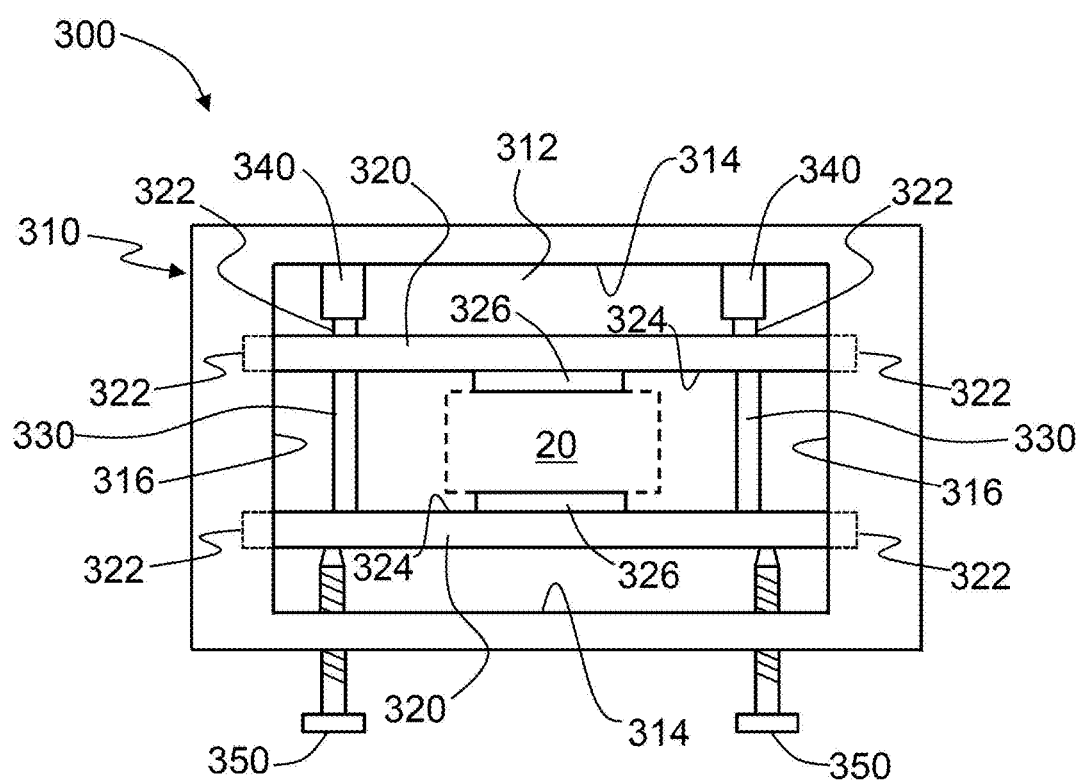
FIG. 8 is a top-down view of an example alignment fixture used to hold and align a curved part of limited diameter and limited length within the prism-coupling system of FIG. 2.

FIG. 8 is a top-down view of an example alignment fixture 300 used to hold and align curved part 20 relative to coupling prism 40. The alignment fixture 300 is configured to interface with coupling-prism assembly 38. The alignment fixture 300 includes a rectangular outer frame 310 having an interior 312 defined by opposing vertical inner sidewalls 314 and opposing horizontal inner sidewalls 316. The alignment fixture 300 includes spaced apart and parallel horizontal guide members 320 that are arranged within frame interior 312 and that have ends 322 configured to slide along or within vertical inner sidewalls 314 (e.g., in tracks, not shown). The horizontal guide members 320 have opposing inner surfaces 324.

The alignment fixture 300 also includes vertically arranged support posts 330 that are fixed to the lower guide member 320 and that pass through the upper support member so that the latter can be translated vertically along the support posts. Each support post 330 has an end 332 that interfaces with respective resilient members 340 on the top vertical inner sidewall 314 of frame 310. The inner surfaces 324 of horizontal guide members 320 include resilient members 326 that are used to engage outer surface 24 of curved part 20 without damaging the curved part. An example cylindrical curved part 20 (dashed lined) is shown being held by resilient members 326.

The alignment fixture 300 also includes alignment screws 350 that pass through a threaded section of outer frame 310 to engage the lower support member 320. The alignment screws 350 can be used to urge the lower support member 320 toward the upper support member, thereby squeezing curved part 20 between resilient members 326. The resilient members 340 allow for the upward movement of lower support member 320 by compressing while also serving as force buffers for impeding the upper support member from moving upward, thus keeping the part aligned along the direction dictated by the screws 350. The alignment screws 350 can also be used to provide a select orientation of curved part 20 within frame interior 312 and thus with respect to coupling prism 40 when alignment fixture 300 is interfaced with coupling-prism assembly 38.

To reduce the coupling between rotation and lateral shift of curved part 20, alignment fixture 300 may be positioned such that coupling prism 40 and the curved part are significantly closer to one of the alignment screws 350 than to the other. In this way the closer alignment screw 350 enables primarily sideways shifting of curved part 20 with respect to the illuminated strip on prism, while the other screw enables primarily rotation with respect to the same illuminated strip. Convergence to optimized positioning and alignment of curved part 20 can occur relatively quickly, e.g., with one to three iterations of using both alignment screws 350. A benefit of using alignment fixture 300 is that it decreases measurement time as compared to manual alignment, particularly when multiple parts of same or similar shape are to be measured sequentially. With use of such an alignment fixture, careful alignment of the first part is enough to ensure quick alignment of all subsequent parts.

Mode-Spectra Broadening Effects

When measuring curved part 20 in the form of an ideal cylinder that is perfectly aligned in coupling-prism assembly 38, minor broadening of the spectral lines of the TE and TE mode spectra is to be expected due to coupling into a bent waveguide with light beam 62F with rays having out-of-plane angles φ. The effective indices of the eigenmodes of a bent waveguide are slightly shifted compared to those of a straight waveguide having an identical cross-section.

The following equation for the effective index shift for a rectangular waveguide can be used to estimate the maximum possible broadening due to this effect:

$$\Delta n_{\mathit{eff}}^{\mathit{bend}} \approx n_0 T/\rho$$

where $n_0$ is the peak refractive index, 2T is the thickness of the rectangular waveguide and $\rho$ is the radius of curvature seen by the obliquely incident ray. For curved part 20, the thickness 2T can be replaced by 0.5·DOL to account for the approximately triangular refractive index profile. For rays impinging on interface 50 in an incidence plane at an, $\rho = R1/\sin^2 \varphi$, where R1 is the cylinder radius. For a 0.5 mm slot, φ ranges from about −10 to +10 degrees (with the maximum angle φ denoted $\varphi_{max}$), although for most of the light the range is from −5 to +5 degrees, so ρ correspondingly takes on values above 1.1 m for R1=8.5 mm. Thus, the broadening effect is:

$$\Delta n_{\mathit{eff}}^{\mathit{bend}} \approx \frac{n_0 DOL}{4\rho} \leq \frac{n_0 DOL}{4R} \sin^2 \varphi_{max} = \frac{1.5 \times 50 \ \mu m}{4 \times 1.1 \ m} \approx 2 \times 10^{-5}$$

This level of line broadening is comparable to the narrowest lines observed with the FSM-6000LE measurement system, whose breadth is limited by either by optical resolution or by the leaky nature of the modes in the measurement. This explains why the systems and methods disclosed herein can be used to measure curved parts 20 having a first radius R1 as small as 1 mm. The broadening in this case would be on the order of $2 \times 10^{-4}$, which barely approaches the minimum mode spacing. This broadening is important only for curved parts 20 having a small radius R1 (e.g., R1<2 mm) and a large DOL, and is mitigated by using a narrower slot.

The above estimates of mode spectra broadening can be turned around and used to determine the slot width required to limit the broadening effect to a desired value. The allowed broadening is smaller than about ⅓ of the typical mode spacing $\Delta n_{ms}$, which in many cases of practical interest is about $5 \times 10^{-4}$ RIU. Then the angular range Δφ in radians allowable by the slot is:

$$\Delta \varphi = 2 \mathrm{asin} \left[ \sqrt{\frac{R1}{\rho}} \right] = 2 \mathrm{asin} \left[ \sqrt{\frac{4 R1 \Delta n_{bend}^{\mathit{eff}}}{n_0 DOL}} \right] = 2 \mathrm{asin} \left[ \sqrt{\frac{4 R1 \Delta n_{ms}}{3 n_0 DOL}} \right]$$

In many cases the typical mode spacing is inversely proportional to DOL. In an example ion exchanged region 25 having maximum index increment of about $1.5 \times 10^{-2}$ RIU, each increment of DOL by about 2 µm adds an extra mode to the spectrum, so a typical mode spacing is on the order of $$\Delta n_{typ} \approx \left(\frac{2}{DOL}\frac{\pi m}{}\right)10^{-2} RIU.$$

Hence, the angular range $\Delta\varphi$ to be allowed by the light restrictor should be no greater than:

$$\Delta\varphi = 2a\sin\left[\sqrt{\frac{4}{3}\frac{R1}{DOL}\frac{\Delta n_{ms}}{n_0}}\right] \approx 2a\sin\left[\sqrt{\frac{4}{3n_0}\frac{R1}{DOL}\frac{2\times10^{-2}}{DOL/\mu m}}\right],$$

In an example, for R1=10 mm, DOL=50 µm, and $n_0 \approx 1.52$, $\Delta\varphi \approx 0.54$ rad $\approx 31°$, so that $\varphi$ should be smaller than about 15°. This is the limit where the line broadening will lead to substantial merging of the lines that would render their resolving impractical. Even smaller line broadening leads to decrease in line contrast, which leads to significant difficulties in intensity-based discrimination for automated identification of the modes.

A stricter criterion can be applied, $$e.g., \Delta n_{eff}^{bend} \leq \frac{\Delta n_{ms}}{6}$$

to substantially limit such contrast decrease. In this case the angular range $\Delta\varphi$ allowed by the light restrictor should be no greater than:

$$\Delta\varphi = 2a\sin\left[\sqrt{\frac{2}{3}\frac{R1}{DOL}\frac{\Delta n_{ms}}{n_0}}\right] \approx 2a\sin\left[\sqrt{\frac{2}{3n_0}\frac{R1}{DOL}\frac{2\times10^{-2}}{DOL/\mu m}}\right],$$

and $\varphi$ should be no more than about 10° for typical ion exchanged glass with maximum index increment on the order of 0.015 RIU and DOL of 50 µm. Finally, to eliminate the effect of line broadening due to coupling to bent-waveguide modes, in an example the broadening should be below about $2\times10^{-5}$ RIU for a typical high-resolution measurement system, in which case:

$$\Delta\varphi = 2a\sin\left[\sqrt{\frac{4r1}{DOL}\frac{2\times10^{-5}}{n_0}}\right].$$

For curved parts 20 having a range of values for the radius R1, such as for conical surfaces, the value of R1 at the bottom of the range should be taken for conservative estimates for the parameters for light-restricting member(s) 200 based on the disclosed relations. On the other hand, for less conservative estimates, any value typical of the bottom half of the range for R1 may allow adequate performance.

Curved parts 20 wherein R1 is as small as 1 mm in the allowed direction were measured, with R2 being least 100 m to prevent observable spectral line broadening, and at least 20 m to avoid significant measurement degradation. Smaller values of R2 can be tolerated if the prism length in the z-direction (see FIG. 1A) is reduced (e.g., from 12 mm to between 2 and 4 mm) to limit the angular spreading of spectral lines due to undesired bulging.

In an example, the width $w_L$ of illumination region 62L may vary as a function of the length of the illumination region (i.e., z-direction). As noted above, in one example, the slot width s of light restricting member 200 may vary between front and back ends 202 and 206 while still allowing for substantial improvement in mode spectra contrast. In particular, a slot 220 whose width s varies between about (⅔)·s and about (1.5)·s between front and back ends 202 and 206 may lead to similar improvement in contrast as a constant-width slot.

It will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A method for determining at least one characteristic of a curved part having a curved outer surface and a near-surface waveguide region defined by an ion-exchanged region, comprising:
    interfacing a coupling surface of a coupling prism to the curved outer surface to define a coupling interface proximate the near-surface waveguide region;
    directing measurement light through the coupling prism and to the coupling interface and coupling a portion of the measurement light into TE and TM modes supported by the near-surface waveguide region, wherein the measurement light has a width of 3 mm or less;
    digitally capturing TE and TM mode spectra reflected from the coupling interface and defined by the TE and TM modes supported by the near-surface waveguide region; and
    processing the TE and TM mode spectra to determine the at least one characteristic of the curved part.

2. The method according to claim 1, wherein the at least one characteristic is selected from the group of characteristics comprising: surface stress, stress profile, compressive stress, depth of layer, refractive index profile, and birefringence.

3. The method according to claim 1, wherein the coupling prism has input and output surfaces, and further comprising:
    directing the measurement light through at least one light-restricting member operably arranged relative to at least one of the input and output surfaces, wherein the at least one light-restricting member includes a slot having either a constant or a varying width, wherein the slot defines the width of the measurement light.

4. The method according to claim 1, wherein the coupling prism has input and output surfaces, and further comprising:
    directing the measurement light through first and second light restricting members disposed adjacent the input and output surfaces respectively, the first and second light restricting members respectively having first and second slots that have either a constant or a varying width, wherein the first and second slots define the width of the measurement light.

5. The method according to claim 1, wherein the input and output surfaces include respective opaque sections that define the width of the measurement light.

6. The method according to claim 1, wherein the coupling surface includes a cylindrically curved portion that substantially matches a curvature of the curved outer surface.

7. The method according to claim 6, wherein the cylindrically curved portion of the coupling surface is defined by a removable cylindrical lens.

8. The method according to claim 1, wherein the curved part is cylindrical and has a first radius of curvature $R1 \geq 0.5$ mm.

9. The method according to claim 1, wherein the coupling prism has a width of 3 mm or less and is operably supported by opaque blocks.

10. The method according to claim 1, including supporting the curved part in an adjustable alignment fixture to align the curved part with the coupling prism.

11. A method for determining at least one characteristic of a curved part having a curved outer surface and a near-surface waveguide region defined by an ion-exchanged region, comprising:
   directing focused measurement light to a coupling-prism assembly having a coupling prism interfaced with the outer surface of the curved part to define a coupling interface, wherein the curved outer surface is defined by a radius $R1 \geq 0.5$ mm and a radius $R2 \geq 20$ m;
   reflecting a portion of the measurement light from the coupling interface and coupling portion of the light into TE and TM modes supported by the near-surface waveguide region, while restricting the measurement light to have a width of 3 mm or less prior to said reflecting;
   detecting the reflected measurement light to obtain TE and TM mode spectra; and
   processing the TE and TM mode spectra to determine the at least one characteristic of the curved part.

12. The method according to claim 10, wherein said restricting is accomplished by one of:
   a) at least one light-restricting member operably arranged relative to the coupling prism and having a slot having a width 3 mm or less through which the measurement light passes;
   b) opaque members that support the coupling prism, wherein the coupling prism has a width of 3 mm or less; and
   c) opaque sections on input and output surfaces that define a slot having a width of 3 mm or less through which the measurement light passes.

13. A prism-coupling system for determining at least one characteristic of a curved part having a curved outer surface and a near-surface waveguide region defined by an ion-exchanged region and that supports TE and TM modes that respectively define TE and TM mode spectra, comprising:
   a light-source system that generates measurement light;
   a coupling-prism assembly having a coupling prism with input and output surfaces and a coupling surface that interfaces with the curved outer surface to define a coupling interface proximate the near-surface waveguide region to couple a portion of the measurement light into the TE and TM modes and to reflect a portion of the measurement light from the coupling interface, wherein the coupling-prism assembly comprises means for defining a width of the measurement light to be 3 mm or less;
   a detector system arranged to receive the portion of the measurement light reflected from the coupling interface and that exits the output surface to digitally capture TE and TM mode spectra; and
   a controller that processes the TE and TM mode spectra to determine the at least one characteristic of the curved part.

14. The system according to claim 13, wherein the at least one characteristic is selected from the group of characteristics comprising: surface stress, stress profile, compressive stress, depth of layer, refractive index profile and birefringence.

15. The system according to claim 13, wherein the coupling-prism assembly comprises
   at least one light-restricting member operably arranged relative to at least one of the input and output surfaces, wherein each light-restricting member includes a slot that defines the width of the measurement light.

16. The system according to claim 13 wherein the input and output surfaces of the coupling prism include respective opaque sections that define the width of the measurement light.

17. The system according to claim 13, wherein the coupling surface includes a cylindrically curved portion that substantially matches a curvature of the curved outer surface.

18. The system according to claim 17, wherein the cylindrically curved portion of the coupling surface is defined by a removable cylindrical lens.

19. The system according to claim 13, wherein the curved part is cylindrical and has a first radius of curvature $R1 \geq 0.5$ mm.

20. The system according to claim 13, further comprising an adjustable alignment fixture that supports the curved part in alignment with the coupling prism.

\* \* \* \* \*

UNITED STATES PATENT AND TRADEMARK OFFICE
CERTIFICATE OF CORRECTION

PATENT NO. : 10,156,488 B2
APPLICATION NO. : 14/013481
DATED : December 18, 2018
INVENTOR(S) : Anping Liu et al.

Page 1 of 1

It is certified that error appears in the above-identified patent and that said Letters Patent is hereby corrected as shown below:

On the Title Page

On page 2, Column 2, item (56), other publications, Line 2, delete "Agricultrual" and insert -- Agricultural --, therefor.

On page 2, Column 2, item (56), other publications, Line 5, delete "Opinoin" and insert -- Opinion --, therefor.

On page 2, Column 2, item (56), other publications, Line 40, delete "Theroy" and insert -- Theory --, therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*